US010289749B2

(12) United States Patent
Payton

(10) Patent No.: US 10,289,749 B2
(45) Date of Patent: May 14, 2019

(54) DEGREE OF SEPARATION FOR MEDIA ARTIFACT DISCOVERY

(75) Inventor: Tirrell Payton, Longwood, FL (US)

(73) Assignee: OATH INC., New York, NY (US)

(*) Notice: Subject to any disclaimer, the term of this patent is extended or adjusted under 35 U.S.C. 154(b) by 1573 days.

(21) Appl. No.: 11/897,051

(22) Filed: Aug. 29, 2007

(65) Prior Publication Data
US 2009/0063973 A1 Mar. 5, 2009

(51) Int. Cl.
G06F 17/30 (2006.01)

(52) U.S. Cl.
CPC .. G06F 17/30905 (2013.01); G06F 17/30029 (2013.01); G06F 17/30867 (2013.01); *A61L 2300/204* (2013.01); *A61L 2300/404* (2013.01); *A61L 2300/416* (2013.01)

(58) Field of Classification Search
CPC ........... G06F 17/3053; G06F 17/30867; G06F 17/30905; G06F 17/30029; G06F 17/30749; G06F 17/30752
USPC .......... 715/745, 708; 707/728, 732, 748–751
See application file for complete search history.

(56) References Cited

U.S. PATENT DOCUMENTS

| | | | |
|---|---|---|---|
| 5,987,454 A * | 11/1999 | Hobbs | |
| 6,338,059 B1 * | 1/2002 | Fields et al. | 715/208 |
| 6,434,556 B1 * | 8/2002 | Levin et al. | |
| 7,000,194 B1 * | 2/2006 | Newbold | 715/789 |
| 7,080,071 B2 * | 7/2006 | Henrion et al. | |
| 7,185,355 B1 * | 2/2007 | Ellis | H04N 5/44543 348/E5.105 |
| 7,257,589 B1 * | 8/2007 | Hull et al. | 707/608 |
| 7,496,583 B2 * | 2/2009 | Moore et al. | |
| 7,512,549 B1 * | 3/2009 | Morita et al. | 705/26 |
| 7,512,900 B2 * | 3/2009 | Lynch et al. | 715/825 |
| 7,519,589 B2 * | 4/2009 | Charnock et al. | |
| 7,565,630 B1 * | 7/2009 | Kamvar et al. | |
| 7,664,746 B2 * | 2/2010 | Majumder | 707/732 |
| 7,680,959 B2 * | 3/2010 | Svendsen | 709/248 |
| 7,693,836 B2 * | 4/2010 | Brave et al. | 709/224 |
| 7,716,223 B2 * | 5/2010 | Haveliwala et al. | 707/738 |
| 7,743,347 B2 * | 6/2010 | Graham et al. | 715/863 |
| 7,747,611 B1 * | 6/2010 | Milic-Frayling et al. | 707/722 |
| 2002/0069223 A1 * | 6/2002 | Goodisman et al. | 707/513 |
| 2002/0082901 A1 * | 6/2002 | Dunning et al. | 705/10 |
| 2002/0083101 A1 * | 6/2002 | Card et al. | 707/526 |
| 2002/0143991 A1 * | 10/2002 | Chow | H04L 29/06 709/245 |
| 2003/0014415 A1 * | 1/2003 | Weiss et al. | 707/10 |
| 2003/0052913 A1 * | 3/2003 | Barile | 345/745 |
| 2003/0079179 A1 * | 4/2003 | Brown et al. | 715/501.1 |
| 2003/0089218 A1 * | 5/2003 | Gang et al. | 84/615 |

(Continued)

Primary Examiner — Amy Ng
Assistant Examiner — William Wong
(74) Attorney, Agent, or Firm — James J. DeCarlo; Greenberg Traurig, LLP

(57) ABSTRACT

Methods and apparatus, including computer program products, for degree of separation for media artifact discovery. A method includes visually highlighting a media artifact on a Web page in response to a user's media preferences and how distant from a core range of media preferences the user wants to engage more media, and generating for display to the user additional information and resources about the visually highlighted media artifact and how the visually highlighted media artifact relates to the core range of media preferences in response to a user action.

22 Claims, 9 Drawing Sheets

(56) References Cited

U.S. PATENT DOCUMENTS

| | | |
|---|---|---|
| 2003/0101104 A1* | 5/2003 | Dimitrova et al. ............ 705/27 |
| 2003/0101413 A1* | 5/2003 | Klein et al. .................. 715/513 |
| 2004/0080532 A1* | 4/2004 | Cragun et al. ................ 345/745 |
| 2004/0183815 A1* | 9/2004 | Ebert ................ G06F 17/3061 345/619 |
| 2004/0215657 A1* | 10/2004 | Drucker et al. ........... 707/104.1 |
| 2005/0010863 A1* | 1/2005 | Zernik .......................... 715/511 |
| 2005/0038775 A1* | 2/2005 | Haveliwala et al. ............. 707/3 |
| 2005/0076241 A1* | 4/2005 | Appelman ..................... 713/201 |
| 2005/0171954 A1* | 8/2005 | Hull et al. ...................... 707/10 |
| 2005/0216434 A1* | 9/2005 | Haveliwala et al. ............. 707/1 |
| 2005/0240661 A1* | 10/2005 | Heller et al. .................. 709/219 |
| 2005/0256866 A1* | 11/2005 | Lu et al. ........................... 707/5 |
| 2006/0004892 A1* | 1/2006 | Lunt et al. ..................... 707/204 |
| 2006/0020596 A1* | 1/2006 | Liu et al. .......................... 707/6 |
| 2006/0047725 A1* | 3/2006 | Bramson ..................... 707/204 |
| 2006/0048060 A1* | 3/2006 | Mohr et al. ................... 715/747 |
| 2006/0053382 A1* | 3/2006 | Gardner et al. ............... 715/764 |
| 2006/0085515 A1* | 4/2006 | Kurtz et al. .................. 709/207 |
| 2006/0150087 A1* | 7/2006 | Cronenberger et al. ....... 715/513 |
| 2006/0156222 A1* | 7/2006 | Chi et al. ..................... 715/512 |
| 2006/0195790 A1* | 8/2006 | Beaupre et al. .............. 715/727 |
| 2006/0235873 A1* | 10/2006 | Thomas ........................ 707/102 |
| 2006/0253771 A1* | 11/2006 | Baschy .......................... 715/500 |
| 2006/0265421 A1* | 11/2006 | Ranasinghe et al. ....... 707/104.1 |
| 2006/0271526 A1* | 11/2006 | Charnock et al. ................ 707/3 |
| 2007/0064626 A1* | 3/2007 | Evans ................ G06F 17/3089 370/254 |
| 2007/0112758 A1* | 5/2007 | Livaditis ........................... 707/5 |
| 2007/0112792 A1* | 5/2007 | Majumder .................... 707/100 |
| 2007/0118803 A1* | 5/2007 | Walker et al. ................ 715/744 |
| 2007/0130276 A1* | 6/2007 | Zhang et al. ................. 709/207 |
| 2007/0162298 A1* | 7/2007 | Melton et al. ................... 705/1 |
| 2007/0203906 A1* | 8/2007 | Cone et al. ....................... 707/6 |
| 2007/0233692 A1* | 10/2007 | Lisa et al. ...................... 707/10 |
| 2007/0260580 A1* | 11/2007 | Omoigui ........................... 707/2 |
| 2008/0005282 A1* | 1/2008 | Gaedcke ........... G06F 17/30867 709/219 |
| 2008/0005664 A1* | 1/2008 | Chandra ....................... 715/513 |
| 2008/0010294 A1* | 1/2008 | Norton et al. .................. 707/10 |
| 2008/0016205 A1* | 1/2008 | Svendsen ..................... 709/224 |
| 2008/0028302 A1* | 1/2008 | Meschkat ................ G06F 8/38 715/255 |
| 2008/0056574 A1* | 3/2008 | Heck ............................. 382/177 |
| 2008/0072145 A1* | 3/2008 | Blanchard et al. ........... 715/273 |
| 2008/0162275 A1* | 7/2008 | Logan et al. ................... 705/12 |
| 2008/0177773 A1* | 7/2008 | Boss et al. .................... 707/102 |
| 2008/0183694 A1* | 7/2008 | Cane et al. ........................ 707/5 |
| 2008/0201434 A1* | 8/2008 | Holmes et al. ............... 709/206 |
| 2008/0229218 A1* | 9/2008 | Maeng .......................... 715/760 |
| 2008/0270449 A1* | 10/2008 | Gossweiler ....... G06F 17/30817 |
| 2009/0019488 A1* | 1/2009 | Ruiz-Velasco ......... G06F 3/0482 725/43 |

\* cited by examiner

KRS-ONE 82

| Song 84 | | Album 86 | Artist 88 | Duration 90 | My Rating 92 | My degree of separation 94 |
|---|---|---|---|---|---|---|
| Rappaz R. N. Dainja | ▶ | Krs One | Krs-One | 5:55 | ⊘✩✩✩✩✩ | 2 |
| De Automatic | ▶ | Krs One | Krs-One | 4:26 | ⊘✩✩✩✩✩ | 1 |
| ☐ MC's Act Like They Do... | ▶ | Krs One | Krs-One | 4:56 | ⊘✩✩✩✩✩ | 1 |
| Ah-Yeah | ▶ | Krs One | Krs-One | 3:51 | ⊘✩✩✩✩✩ | 0 |
| R.E.A.L.I.T.Y. | ▶ | Krs One | Krs-One | 4:15 | ⊘✩✩✩✩✩ | 1 |
| Free Mumia | ▶ | Krs One | Krs-One | 4:19 | ⊘✩✩✩✩✩ | 2 |
| Hold | ▶ | Krs One | Krs-One | 5:55 | ⊘✩✩✩✩✩ | 2 |
| Wannabemceez | ▶ | Krs One | Krs-One | 4:22 | ⊘✩✩✩✩✩ | 2 |
| Represent The Real Hi... | ▶ | Krs One | Krs-One | 4:39 | ⊘✩✩✩✩✩ | 2 |
| The Truth | ▶ | Krs One | Krs-One | 3:47 | ⊘✩✩✩✩✩ | 1 |
| Build Ya Skillz | ▶ | Krs One | Krs-One | 4:42 | ⊘✩✩✩✩✩ | 2 |
| Out For Fame | ▶ | Krs One | Krs-One | 4:53 | ⊘✩✩✩✩✩ | 2 |
| Squash All Beef | ▶ | Krs One | Krs-One | 5:04 | ⊘✩✩✩✩✩ | 2 |
| Health, Wealth, Self | ▶ | Krs One | Krs-One | 4:58 | ⊘✩✩✩✩✩ | 2 |

DEGREE OF SEPARATION FOR MEDIA ARTIFACT DISCOVERY

BACKGROUND

The present invention relates to data processing by digital computer, and more particularly to degree of separation for media artifact discovery.

The World Wide Web (the "Web") is a system of interlinked, hypertext documents accessed using the Internet. A Web browser, often considered a client program in a client server network, is an application program that provides a way to look at and interact with all the information (generally referred to as "content") on the Web. With a Web browser, such as Firefox®, Opera®, or Netscape Navigator®, a user can view Web pages that may contain text, images, and/or other multimedia, and navigate between Web pages using hyperlinks.

With the plethora of content residing on the Web, it is often difficult, time consuming and sometimes less than apparent for a user to narrow the tsunami of information and be exposed to new content with some relationship to the user's personal tastes and preferences.

SUMMARY

The present invention provides methods and apparatus, including computer program products, for degree of separation for media artifact discovery.

In general, in one aspect, the invention features a method including visually highlighting a media artifact on a Web page in response to a user's media preferences and how distant from a core range of media preferences the user wants to engage more media, and generating for display to the user additional information and resources about the visually highlighted media artifact and how the visually highlighted media artifact relates to the core range of media preferences in response to a user action.

In embodiments, the media artifact can be selected from the group including movie titles, actors, audio artists, album titles, publications, song titles and singers.

Visually highlighting can include altering an appearance of the media artifact. Altering can include underlining and/or bolding the media artifact.

The user's media preferences can be selected from the group including preferred movie titles, preferred actors, preferred audio artists, preferred album titles, preferred publications, preferred song titles and preferred singers.

The core range of media preferences can include a numerical indication representing a range of information that is tangential to a primary media preference in which the user may be interested.

Generating can include matching the media artifact against the user's media preferences and the core range of media preferences with data in a store of media artifact information, the matching including identifying one or more relationships between the media artifact against the user's media preferences, the core range of media preferences and the data in the store.

The method can include displaying the generated additional information and resources about the visually highlighted media artifact and how the visually highlighted media artifact relates to the core range of media preferences in a pop-up window. The method can include visually highlighting a media artifact in the pop-up window in response to the user's media preferences and how distant from a core range of media preferences the user wants to engage more media, and generating for display to the user additional information and resources about the visually highlighted media artifact and how the visually highlighted media artifact relates to the core range of media preferences in response to a user action. Displaying can include the generated additional information and resources about the visually highlighted media artifact and how the visually highlighted media artifact relates to the core range of media preferences in a second pop-up window.

The user action can be selected from the group including mouse movement, mouse clicking, keyboard input and touch input.

In another aspect, the invention features a method including, in a network of interconnected computers, storing information related to media artifacts on a server, storing a user's media preferences and how distant from a core range of media preferences the user wants to engage more media on the server, visually highlighting a media artifact on a Web page in response to a user's media preferences and how distant from a core range of media preferences the user wants to engage more media, and generating for display to the user additional information and resources about the visually highlighted media artifact and how the visually highlighted media artifact relates to the core range of media preferences in response to a user action, the user action selected from the group including mouse movement, mouse clicking, keyboard input and touch input.

In embodiments, the media artifacts can be selected from the group including movie titles, actors, audio artists, album titles, publications, song titles and singers.

Visually highlighting can include altering an appearance of the media artifact. Altering can include underlining and/or bolding the media artifact.

The user's media preferences can be selected from the group including preferred movie titles, preferred actors, preferred audio artists, preferred album titles, preferred publications, preferred song titles and preferred singers.

The core range of media preferences including a pictorial indication representing a range of information that is tangential to a primary media preference in which the user may be interested.

Generating can include matching the media artifact against the user's media preferences and the core range of media preferences with data in the store of media artifact information, the matching including identifying one or more relationships between the media artifact against the user's media preferences, the core range of media preferences and the data in the store.

The method can include displaying the generated additional information and resources about the visually highlighted media artifact and how the visually highlighted media artifact relates to the core range of media preferences in a pop-up window, visually highlighting a media artifact in the pop-up window in response to the user's media preferences and how distant from a core range of media preferences the user wants to engage more media, and generating for display to the user additional information and resources about the visually highlighted media artifact and how the visually highlighted media artifact relates to the core range of media preferences in response to a user action. The method can include displaying the generated additional information and resources about the visually highlighted media artifact and how the visually highlighted media artifact relates to the core range of media preferences in a second pop-up window.

In another aspect, the invention features a method including, in a network, sending user media preferences relating to media artifacts and how distant from a core range of media preferences a user wants to engage more media from a client to a server, loading a web page on the client, the web page including a visually highlighted media artifact, activating the visually highlighted media artifact on the web page, and in response to activating, receiving additional information and resources about the visually highlighted media artifact and how the visually highlighted media artifact relates to the user media preferences from the server for display to the user.

In embodiments, the media artifacts can be selected from the group including movie titles, actors, audio artists, album titles, publications, song titles and singers.

The distance from a core range of media preferences can include a numerical indication representing a range of information that can be tangential to a primary media preference in which the user may be interested.

The visually highlighted media artifact can include a match among the media artifact, the user's media preferences, the core range of media preferences and data in a store of media artifact information in the server.

The received additional information and resources about the visually highlighted media artifact and how the visually highlighted media artifact relates to the user media preferences can be displayed in a pop-up window.

The method can include activating a visually highlighted media artifact on the pop-up window, and in response to activating, receiving additional information and resources about the visually highlighted media artifact in the pop-up window and how the visually highlighted media artifact relates to the user media preferences from the server for display to the user.

The received additional information and resources about the visually highlighted media artifact in the pop-up window and how the visually highlighted media artifact relates to the user media preferences can be displayed in a second pop-up window.

In another aspect, the invention features a graphical user interface (GUI) including a display including user-selectable media artifacts, user-selectable ratings of the media artifacts, and user-selectable preference indicators preference including a numerical indication of how distant from a core range of media preferences a user wants to engage more media.

In embodiments, the media artifacts can be selected from the group including movie titles, actors, audio artists, album titles, publications, song titles and singers.

The ratings can be selected from the group including numerical indicators and pictorial indicators.

The invention can be implemented to realize one or more of the following advantages.

A method solves the problem of new media discovery by leveraging institutional and social knowledge in conjunction with context and user preferences.

A method reads a media artifact and cross references the media artifact against a user's preferences and tastes (e.g., ratings), and how far out of a core range a user wants to engage more media, i.e., degrees of separation. The method pulls more information and resources about the particular media artifact and how it relates to the core preferences of the user.

A method enables a greatly enhanced and near seamless media discovery experience.

A method leverages "the world's knowledge" contained as content on a globally connected network of computers to provide a wide range of resources for a particular media artifact.

One implementation of the invention provides all of the above advantages.

Other features and advantages of the invention are apparent from the following description, and from the claims.

BRIEF DESCRIPTION OF THE DRAWINGS

FIG. 5 is a diagram of an exemplary user preference store.
FIG. 7 is an exemplary Graphical User Interface (GUI).
FIG. 8 is an exemplary GUI.
FIG. 9 is an exemplary GUI.

Like reference numbers and designations in the various drawings indicate like elements.

DETAILED DESCRIPTION

Figure 1:
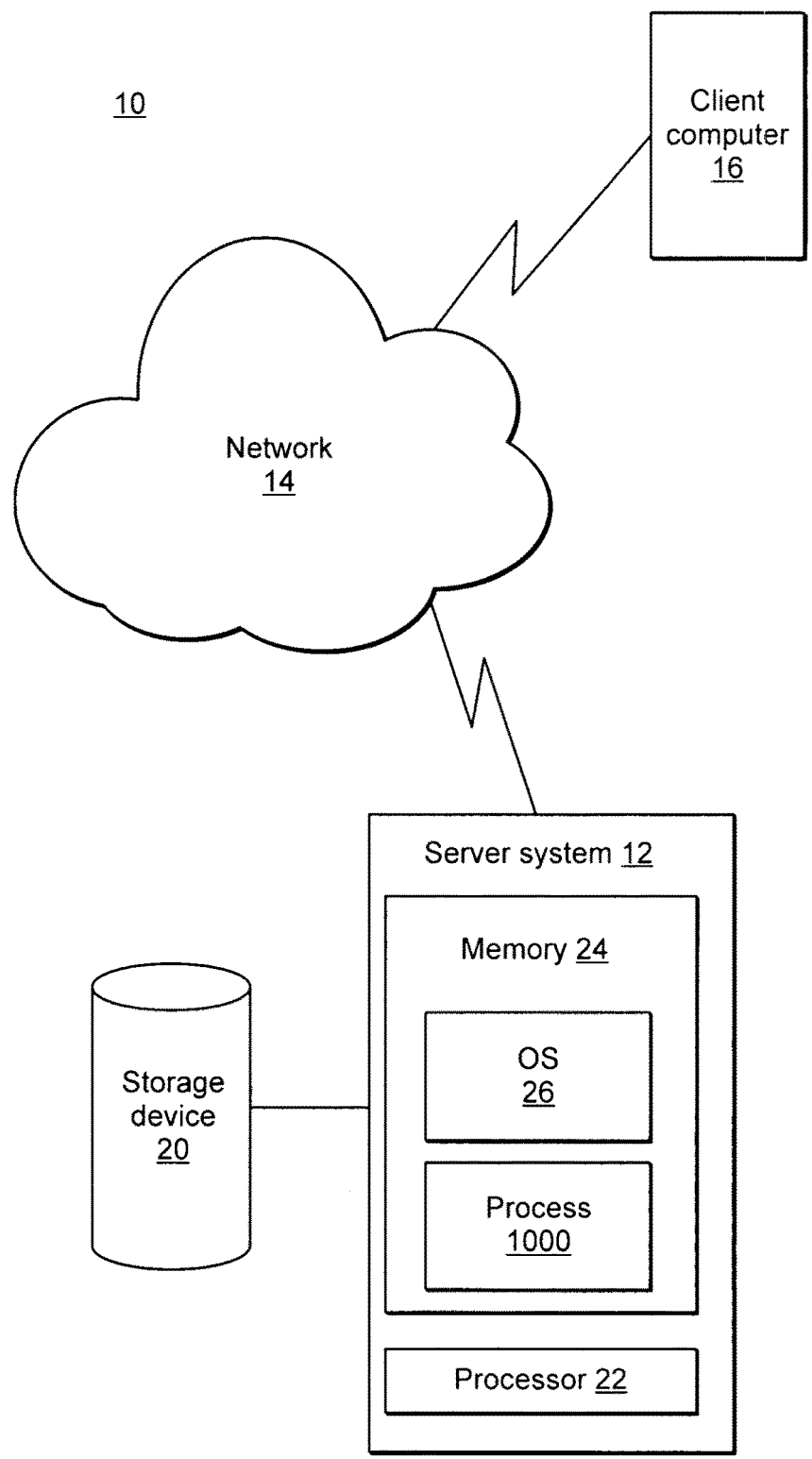
FIG. 1 is a block diagram of an exemplary system.

As shown in FIG. 1, an exemplary system 10, shown here as a client server system, includes a server 12 connected to a global network of interconnected computers 14. A client 16 is linked to the server 12 through the network 14.

The server 12 can include a storage device 20 for storing content and data that is distributed through the network 14 to the client 16. The server 12 includes a processor 22 and memory 24. Memory 24 includes an operating system (OS) 26, such as Linux® or Windows®, and a new media discovery process 1000, described below.

In one particular example, the network 14 is the Internet. In other examples, the network 14 can be any network capable of transmitting data, such as, for example, an intranet, Local Area Network (LAN), Wide Area Network (WAN), or other network using point-to-point protocols (PPP), Wireless Application Protocols (WAP), and so forth.

Figure 2:
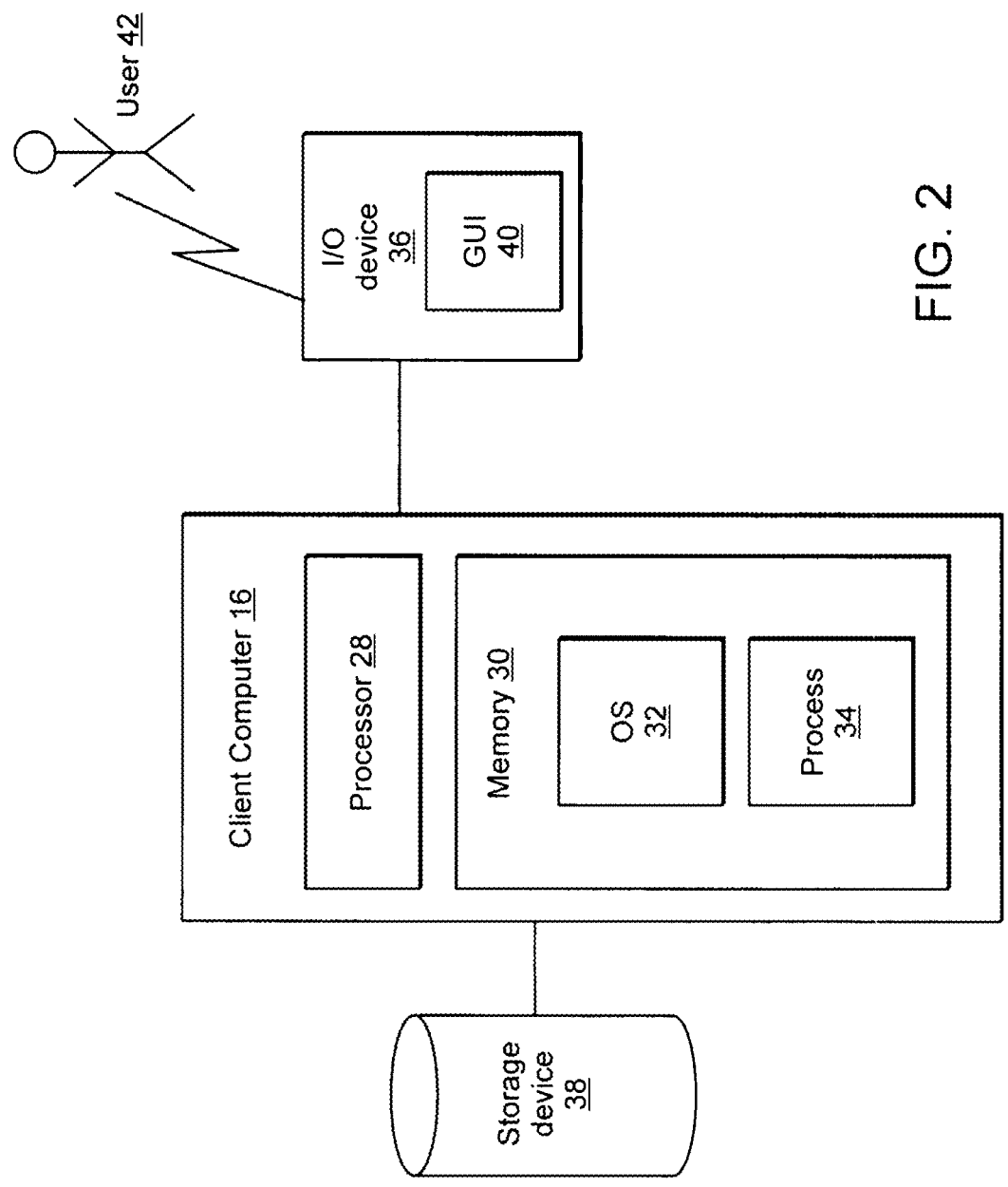
FIG. 2 is a block diagram of an exemplary client.

As shown in FIG. 2, client 16 includes a processor 28 and memory 30. Memory includes an OS 32, such as Linux® or Windows®, and a Web browser process 34, such as Firefox®, Opera® or Netscape Navigator®. A user accesses content residing on the server 12 through network 14 using Web browser process 34. In general, a Web browser is a software application used to locate and display Web pages. Most Web browsers are graphical in nature, which means that they can display graphics as well as text. In addition, most Web browsers can present multimedia information, including sound and video, and some include plug-ins designed for some particular formats and functions.

The client 16 includes an input/output (I/O) device 36 and may include a storage device 38. The I/O device 36 often includes a graphical user interface (GUI) 40, used by the Web browser process 34, for display to a user 42.

Figure 3:
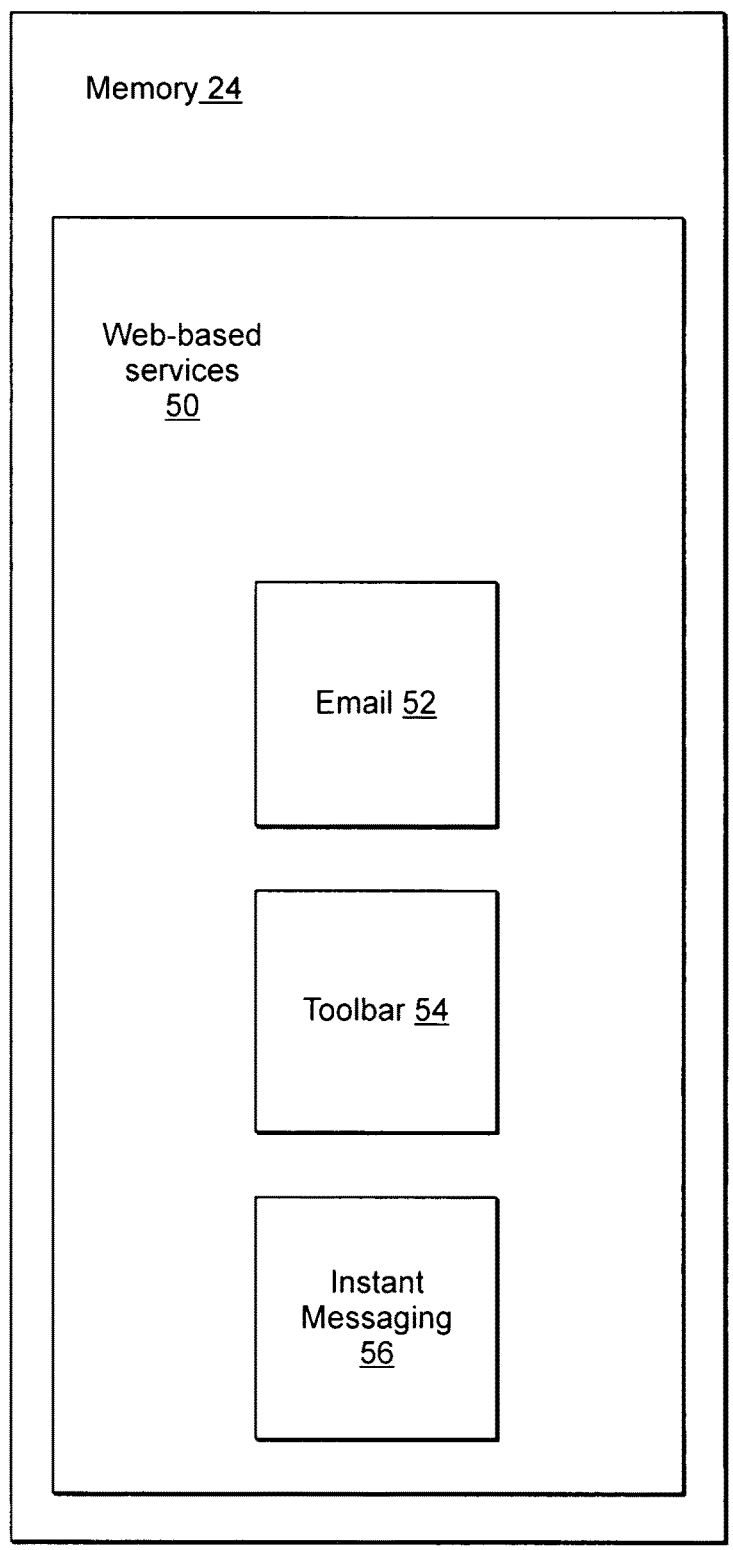
FIG. 3 is a block diagram of an exemplary server.

As shown in FIG. 3, the server 12 can include one or more web-based services 50 that the user 42 of the client 16 may subscribe to. Web-based services 50 can include Web-based email services 52, such as Yahoo!® email, Web-based toolbar services 54, such as Yahoo!® toolbar, Web-based instant messaging services 56, such as Yahoo!® Messenger, and so forth. In general, Web-based email (or "Web mail") is a term that refers to an e-mail service intended to be primarily accessed using the Web browser process 34, as opposed to through an application such as Mozilla's Thunderbird™, Apple's® Mail or Microsoft Outlook®.

In general, a toolbar is a row, column, or block of onscreen buttons or icons that, when clicked, activate certain functions of the toolbar program. Web-based toolbars for Web browsers add functionality and ease-of-use options for the end user. While the Web browser itself handles basic browsing navigation (e.g., "Back," "Stop," "Reload," and so forth), Web-based toolbars often add additional functionality to browsers (e.g., additional search fields, form-fill, links back to popular sites, and so forth).

In general, instant messaging (IM) is a form of real-time communication between two or more people based on typed text. The text is conveyed via computers connected over a network such as the Internet.

Figure 4:
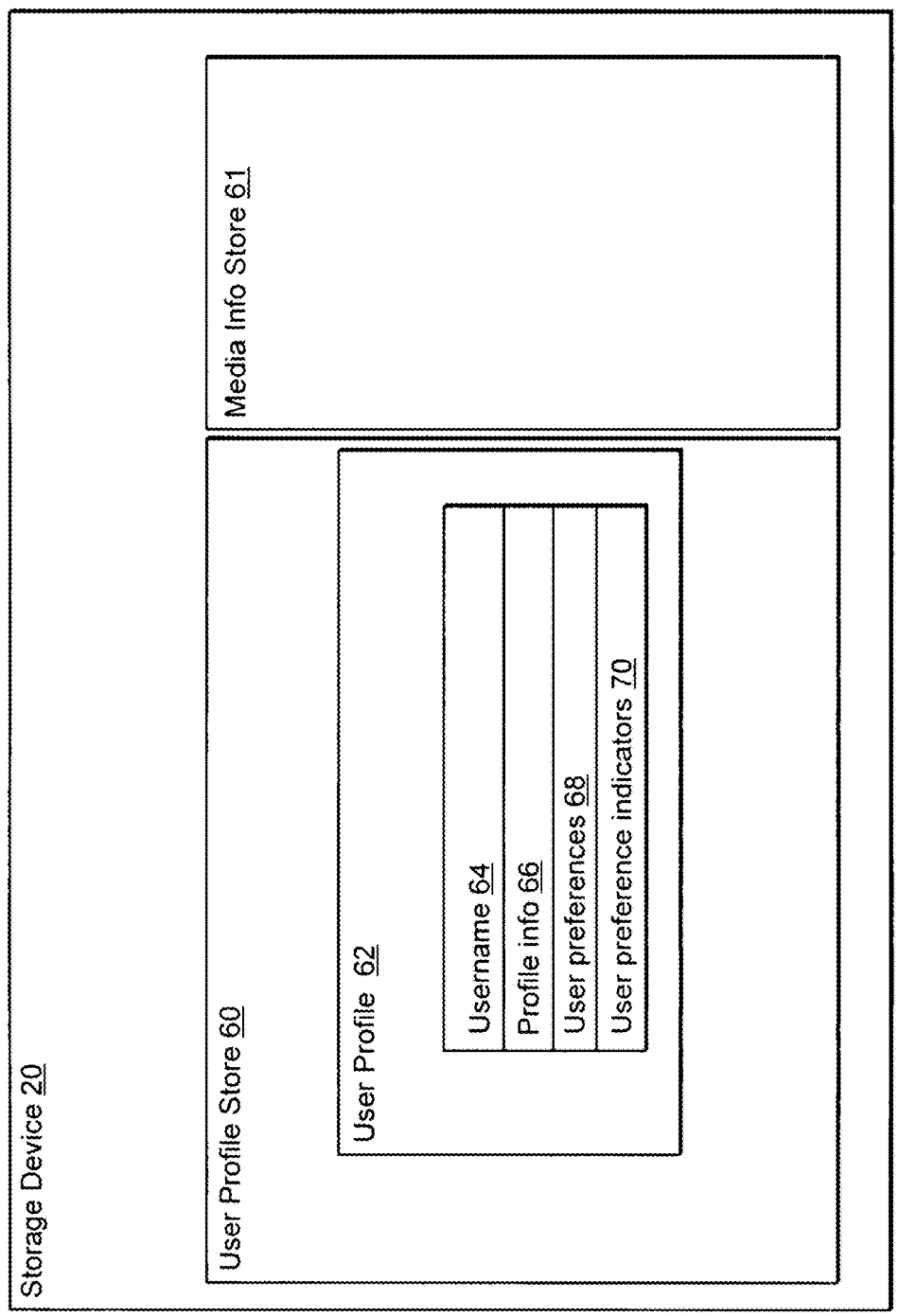
FIG. 4 is a block diagram of an exemplary user profile store and an exemplary media information store.

As shown in FIG. 4, the server 12 can include a user profile store 60 and a media information store 61. The user profile store 60 can be a flat file containing user profile information and user preferences or a database file within a database management system (DBMS). The user profile store 60 includes a user profile 62 for each user registered with one of the web-based services 50. The user profile 62 can include one or more data elements relating to the registered user, such as username 64, profile information 66 (e.g., age range, nationality, sex, geographic residence, and so forth), user preferences 68 (e.g., favorite media artifacts and so forth), and user preference indicators 70. Media artifacts can include, for example, movie titles, actors, audio artists, album titles, publications, song titles and singers.

User preferences 68, sometimes referred to as "core preferences," can include, for example, preferred movie titles, preferred song artists, preferred song titles, preferred album titles, preferred actors, preferred singers, preferred publications and other ancillary information. User preference indicators 70 generally indicate how far out of or away from the core preferences a user may want to discover new media artifacts (sometimes referred to as "degrees of separation"). For example, a user preference may be "action-type" movies. If a user's preference indicators reflect that the user is willing to be exposed to or learn about movies one degree of separation away from action-type movies, process 1000 may consider "mystery-type" movies. If a user's preference indicators reflect that the user is willing to be exposed to or learn about movies two degrees of separation away from action-type movies, process 1000 may include a tertiary indication of "drama-type" movies. In an extreme example, a user preference indicator 70 may indicate the user is unwilling to be exposed to or learn about anything but the user's core preferences (i.e., zero degree of separation).

The media information store 61 includes general media data accumulated by the server 12 in response to search (e.g., crawler) and indexing of server systems (not shown) linked to or residing in the global network of interconnected computers 14. In general, a crawler is a process residing in a server system that visits Web sites and reads their Web pages and other information in order to generate entries for a search engine index. The major search engines on the Web, such as Yahoo!®, all have such a program, which is also known as a "spider" or a "bot." Crawlers are typically programmed to visit Web sites that have been submitted by their owners as new or updated. Entire Web sites or specific Web pages can be selectively visited and indexed.

As shown in FIG. 5, an exemplary user preference 80 indicates a user's preference for the artist KRS-ONE 82. The user preference 80 includes a song title 84, an album title 86, an artist name 88, a duration 90, a user rating 92 and a degree of separation 94. In this example, the user ratings 92 are pictorial, i.e., stars, and the degrees of separation 94 range from 0 to 2.

Figure 6:
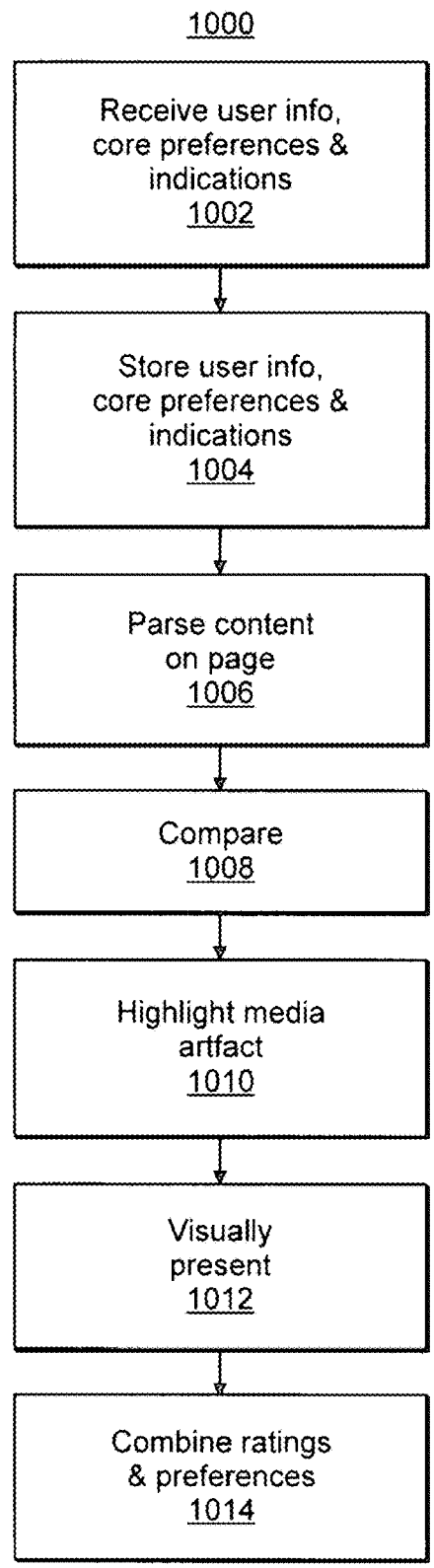
FIG. 6 is a flow diagram of an exemplary new media discovery process.

Process 1000 enables new media discovery by leveraging institutional and social knowledge in conjunction with context and user preferences stored in the user profile store 60 at the server 12. As shown in FIG. 6, new media discovery process 1000 includes receiving (1002) user profile information, user core preferences and indications of how far out of these core preferences the user wants to discover new media (i.e., degrees of separation).

The new media discovery process 1000 stores (1004) the user profile information, user core preferences and indications of how far out of these core preferences the user wants to discover new media (i.e., degrees of separation).

As the user surfs Web pages, the new media discovery process 1000 parses (1006) the content of the Web pages and compares (1008) the parsed content against the stored user profile information, user core preferences and indications of how far out (e.g., degrees of separation) of these core preferences the user wants to discover new media.

Parsing (1006) occurs in the client 16 using a helper application, such as YAHOO!® Toolbar or YAHOO!® browser plus. This helper application communicates with the server 12 in order to find matches of Web content, user preferences and data contained in the media information store 61. Comparing (1008) occurs in the client 16 using the same helper application. The user preferences and degrees of separation are stored in the server 12 in user profile store 60. The helper application obtains preferences and media information from the server 12 in order to know what it needs to visually highlight.

When new media discovery process 1000 finds a media artifact in the media information store 61 that matches the user's preferences and indications, new media discovery process 1000 visually highlights (1010) this media artifact to the user's attention. Visually highlighting (1010) can include underlining, bolding, font size, type or shape change, flashing, or otherwise visually differentiating the media artifact from the other content on the displayed page. Other attention-getting options can include, for example, causing a sound, spoken words, snippet of music, and so forth.

In response to the user rolling a mouse or other indication, such as a click or a touch, over the visually highlighted media artifact, new media discovery process 1000 visually presents (1012) additional information about the media artifact and how this media artifact relates to the user's preferences. In a particular example, presenting (1012) is enabled by JavaScript® injected into the Web page.

In general, JAVASCRIPT® is a scripting language used to write functions that are embedded in or included from Hypertext Markup Language (HTML) Web pages and interact with the Document Object Model (DOM) of the Web page to perform tasks not possible in HTML alone. In this example, presenting (1012) the additional information takes a form of a display pop-up window. The JAVASCRIPT® is injected into the HTML of the page by the helper application (e.g., YAHOO!® Toolbar or YAHOO!® browser plus) that runs in the client 16.

In response to the user clicking on a portion of the additional information, new media discovery process 1000 combines (1014) ratings and preferences to better fine tune the user profile and engage in more media discovery. As described previously, the ratings and preferences are stored on the server 12 in the user preference store 60. When the user clicks, for example, on the presented Javascript®, the Javascript® passes information back to the server 12 and adds this information to the existing user preferences of this particular user that are stored on the server 12. The helper application that runs on the client 16 acts as a middle layer between the Javascript® (i.e., presentation layer) and the server-side 12 information (i.e., database layer). This middle layer processes all of the necessary preferences logic (based on user preference information from the server 12) and controls the discovery and visually highlighting of the media artifacts via the Javascript®. The server 12 that is serving the page is completely independent of this process.

Figure 7:
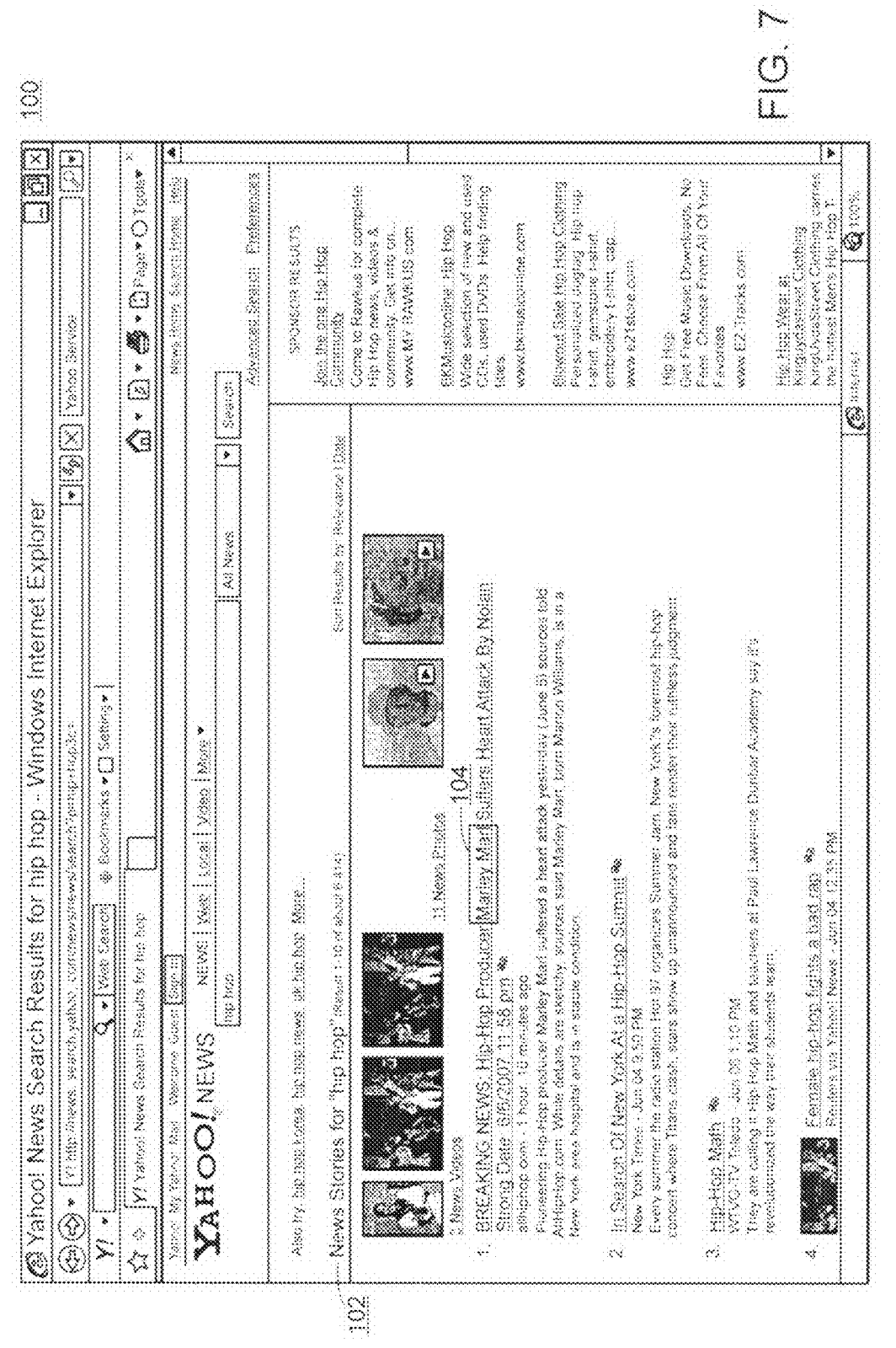

New media discovery process 1000 can be illustrated by way of an example. As shown in FIG. 7, a graphical user interface (GUI) 100 displays some hip hop news 102 and some news about Marley Marl 104. Process 1000 recognizes Marley Marl's name as a media artifact based on this user's preferences but the user is not familiar with Marley Marl's work. This user, for example, has preferences shown previously in FIG. 5. Because Marley Marl has been determined to be of relevance to the user by virtue of the user's stored preference information and the page being parsed to identify media artifacts as described above, the words Marley Marl 104 are visually highlighted in GUI 100.

Figure 8:
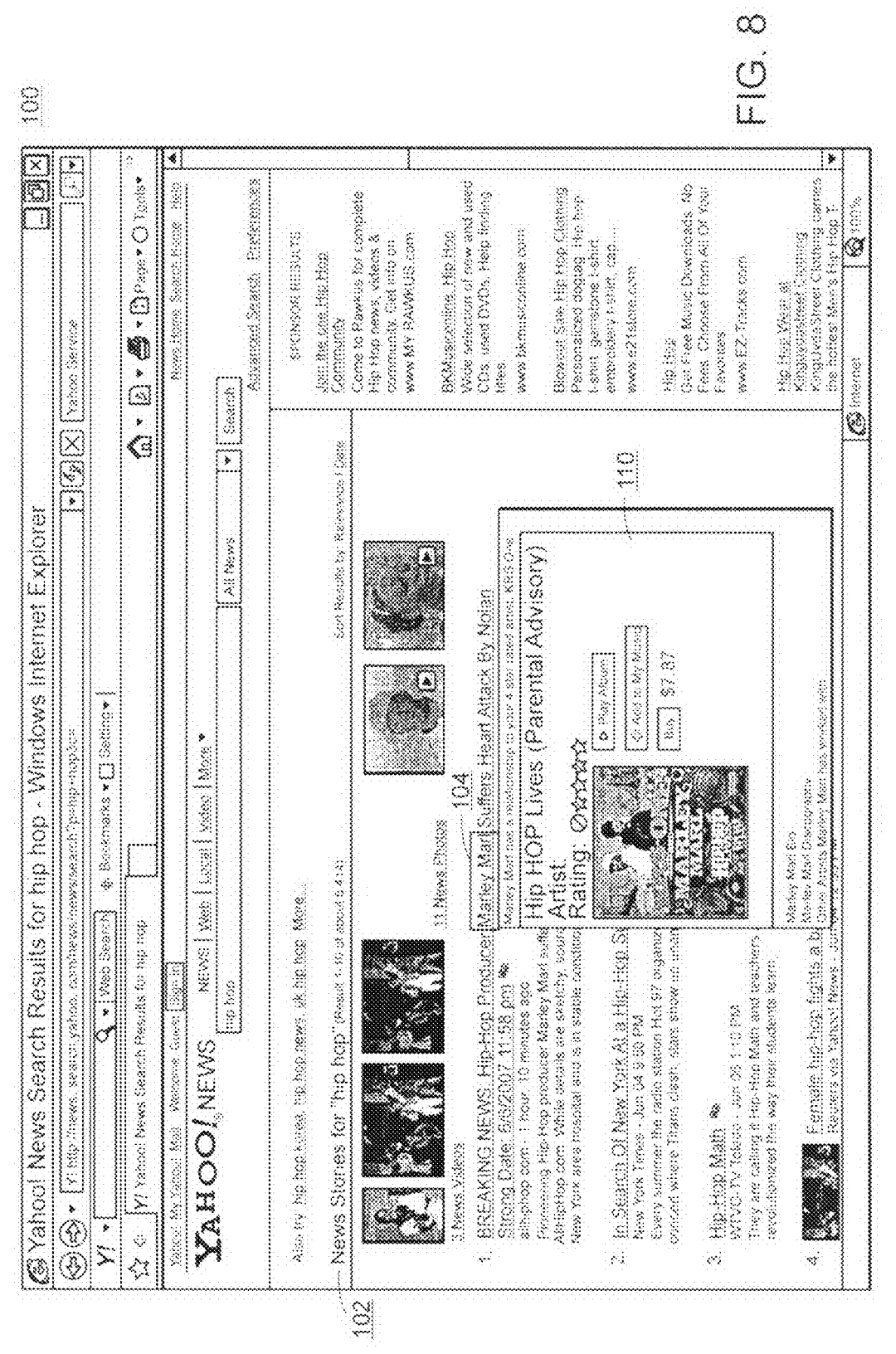

As shown in FIG. 8, process 1000 presents a pop-up window 110 with an album that Marley Marl performed along with KRS-ONE, in response to the user dragging a mouse, for example, over the visually highlighted text 104. From there the user can play the album, add it to user's preferences, rate it, and so forth. Here, the user preferences and user preference indicators are set to "2 degrees of separation" for "all artists rated 4 stars." Since Marley Marl recently performed an album with KRS (i.e., 1 degree), a pop-up window is generated. Preferable, there is more information available to the user on Marley Marl, such as his bio, discography, and other artists he has worked with.

As described above, the user preferences and degrees of separation are set in the general user preferences of that user's profile. As the user navigates and discovers more music or other media artifacts, the user rates more music, and this adds to the server-side store of data about that user (i.e., updates the user profile information stored in the user profile store 60 for this particular user). These degrees are determined by the "directness of the relationship" of one media artifact to another. Using an example of the rock band Led Zepplin, Robert Plant would be 1 degree (band member, direct connection) and Jimmy Page would be 1 degree (band member, direct connection). The rock band the Yardbirds would be 2 degrees (Jimmy Page was in this band before Led Zepplin, secondary connection). Band of Joy would be 2 degrees (Robert Plant was in this band before Led Zepplin, secondary connection). Kevyn Gammond would be 3 degrees (Kevyn Gammond was in Band of Joy, tertiary connection). Chris Dreja would be 3 degrees (Chris Dreja was in the Yardbirds, tertiary connection).

Figure 9:
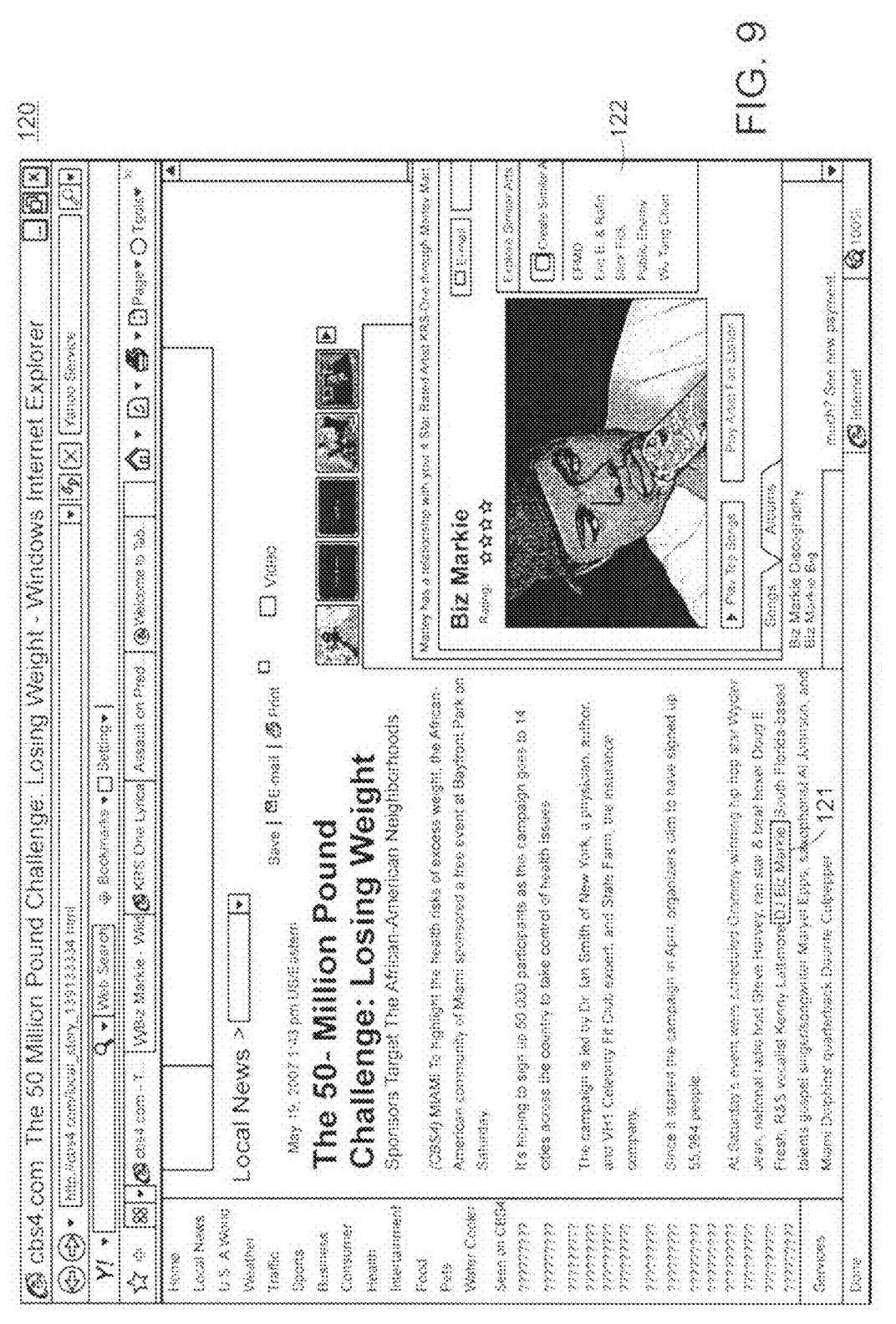

As shown in FIG. 9, a GUI 120 displays an example of a 2.sup.nd degree of separation can occur for the 4 star rated artist KRS-ONE. In this example, Biz Markie has a relationship with the user's 4 star rated artist KRS-ONE through Marl. Assume the user preference indicator is set to 2 degrees of separation for all artists. Biz Markie was produced by Marley Marl as part of the Juice Crew, and Marley Marl recently performed on an album with KRS-ONE, so if the user drags a mouse, for example, over the visually highlighted text 121, process 1000 generates a pop-up window 122. There is more information available to the user in the popup window 122, such as his bio, discography and other artists he has worked with. The user can play, add to their preferences and rate. This is determined and stored at the server 12 using server-based applications, such as Yahoo! As described above, the information gets to the JAVASCRIPT® pop-up by way of the middle layer installed on the client 16. For example, the media artifact can be added to a user's YAHOO!® media storage locker.

Features for a given media artifact include for example, "rate" (i.e., add a rating to the artifact), "store" (e.g., download to from client 16 to YAHOO!® media storage locker on the server 12), "add to playlist" (e.g., adds to playlist that is stored in the YAHOO!® media storage locker), "burn" (e.g., burns to a CD via the middle layer (described above) installed on the client 16), "share via email" (e.g., emails a link to the artifact with additional artifact information), and "save via YAHOO!® Instant Messenger (i.e., Instant Messenger's a link to the artifact with additional artifact information).

Embodiments of the invention can be implemented in digital electronic circuitry, or in computer hardware, firmware, software, or in combinations of them. Embodiments of the invention can be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand alone program or as a module, component, subroutine, or other unit suitable for use in a computing environment. A computer program can be deployed to be executed on one computer or on multiple computers at one site or distributed across multiple sites and interconnected by a communication network.

Method steps of embodiments of the invention can be performed by one or more programmable processors executing a computer program to perform functions, of the invention by operating on input data and generating output. Method steps can also be performed by, and apparatus of the invention can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry.

It is to be understood that the foregoing description is intended to illustrate and not to limit the scope of the invention, which is defined by the scope of the appended claims. Other embodiments are within the scope of the following claims.

What is claimed is:

1. A method comprising:
communicating, by a computing device, media preferences of a particular user to a server, said communicating causing said media preferences to be stored in storage on a network, said media preferences comprising core preferences and at least one numerical indicator indicating a degree of separation that defines how far out additional media is to be identified from the core preferences;
loading, by the computing device, a web page;
executing, upon said loading of the web page by the computing device, a helper application, said executing of the helper application causing the computing device to retrieve said stored media preferences over the network, said executing of the helper application further comprising parsing, via the helper application, said web page, and based on said parsing, identifying content included on said web page, said executing of the helper application further comprising comparing said content to said retrieved media preferences, and based on said comparing, identifying at least one item within said content of the web page as a media artifact;
modifying, via helper application executing on the computing device, said web page based on said identifying of the media artifact, said modifying comprising embedding scripting object code into code of the web page that interacts with a document object model (DOM) of the web page, said modifying causing a visible alteration of the web page comprising modifying a display of the media artifact on the web page based on the embedding of the scripting object code, wherein said visible alteration comprises visually highlighting, underlining, or bolding the media artifact;
receiving, via the computing device, a selection of the displayed media artifact, wherein the selection comprises a user action to the displayed media artifact;
communicating, via the helper application executing on computing device, to the server over the network, a search for additional content based on the media artifact and the media preferences; and
receiving and displaying in a window related to the media artifact, via the computing device, said additional content and an indication as to how far out the additional content is from the core preferences in response to the selection.

2. The method of claim 1 wherein the media artifact is selected from the group consisting of movie titles, actors, audio artists, album titles, publications, song titles and singers.

3. The method of claim 1 wherein said visible alteration comprises visually highlighting the media artifact.

4. The method of claim 3 wherein said visible alteration comprises underlining the media artifact.

5. The method of claim 3 wherein said visible alteration comprises bolding the media artifact.

6. The method of claim 1 wherein the core preferences are selected from the group consisting of preferred movie titles, preferred actors, preferred audio artists, preferred album titles, preferred publications, preferred song titles and preferred singers.

7. The method of claim 1 wherein a core range of media preferences comprises a numerical indication representing a range of information that is tangential to a core preference.

8. The method of claim 1, further comprising: matching the media artifact against the core preferences and the at least one numerical indicator with data in a store of media artifact information, the matching comprising identifying one or more relationships between the media artifact against the core preferences, the at least one numerical indicator and the data in the store.

9. The method of claim 1 further comprising displaying additional information and resources about a visually highlighted media artifact and how the visually highlighted media artifact relates to the media preferences in a pop-up window.

10. The method of claim 9 further comprising: visually highlighting a media artifact in the pop-up window in response to the core preferences and how far out additional media is to be identified from the core preferences; and generating, for display to the user, additional information and resources about the visually highlighted media artifact in the pop-up window and how the visually highlighted media artifact in the pop-up window relates to the media preferences in response to a user action.

11. The method of claim 10 further comprising displaying the generated additional information and resources about the visually highlighted media artifact in the pop-up window and how the visually highlighted media artifact in the pop-up window relates to the media preferences in a second pop-up window.

12. The method of claim 1 wherein the selection comprises user action selected from the group consisting of mouse movement, mouse clicking, keyboard input and touch input.

13. A non-transitory computer-readable storage medium tangibly encoded with a computer program product, that when executed by a processor associated with a computing device, performs a method comprising:
communicating, by the computing device, a media preferences of a particular user to a server, said communicating causing said media preferences to be stored in storage on a network, said media preferences comprising core preferences and at least one numerical indicator indicating a degree of separation that defines how far out additional media is to be identified from the core preferences;
loading, by the computing device, a web page;
executing, upon said loading of the web page by the computing device, a helper application, said executing of the helper application causing the computing device to retrieve said stored media preferences over the network, said executing of the helper application further comprising parsing, via the helper application, said web page, and based on said parsing, identifying content included on said web page, said executing of the helper application further comprising comparing said content to said retrieved media preferences, and based on said comparing, identifying at least one item within said content of the web page as a media artifact;
modifying, via helper application executing on the computing device, said web page based on said identifying of the media artifact, said modifying comprising embedding scripting object code into code of the web page that interacts with a document object model (DOM) of the web page, said modifying causing a visible alteration of the web page comprising modifying a display of the media artifact on the web page based on the embedding of the scripting object code, wherein said visible alteration comprises visually highlighting, underlining, or bolding the media artifact;
receiving, via the computing device, a selection of the displayed media artifact, wherein the selection comprises a user action to the displayed media artifact;

communicating, via the helper application executing on computing device, to the server over the network, a search for additional content based on the media artifact and the media preferences; and receiving and displaying in a window related to the media artifact, via the computing device, said additional content and an indication as to how far out the additional content is from the core preferences in response to the selection.

14. The non-transitory computer-readable storage medium of claim 13 wherein the media artifact is selected from the group consisting of movie titles, actors, audio artists, album titles, publications, song titles and singers.

15. The non-transitory computer-readable storage medium of claim 13 wherein said visible alteration comprises visually highlighting the media artifact.

16. The non-transitory computer-readable storage medium of claim 13 wherein the core preferences are selected from the group consisting of preferred movie titles, preferred actors, preferred audio artists, preferred album titles, preferred publications, preferred song titles and preferred singers.

17. The non-transitory computer-readable storage medium of claim 13 wherein a core range of media preferences comprises a numerical indication representing a range of information that is tangential to a core preference.

18. The non-transitory computer-readable storage medium of claim 13, further comprising: matching the media artifact against the core preferences and the at least one numerical indicator with data in a store of media artifact information, the matching comprising identifying one or more relationships between the media artifact against the core preferences, the at least one numerical indicator and the data in the store.

19. The non-transitory computer-readable storage medium of claim 13 further comprising: displaying the additional information and resources about a visually highlighted media artifact and how the visually highlighted media artifact relates to the media preferences in a pop-up window.

20. The non-transitory computer-readable storage medium of claim 19 further comprising: visually highlighting a media artifact in the pop-up window in response to the core preferences and how far out additional media is to be identified from the core preferences; and generating for display to the user additional information and resources about the visually highlighted media artifact in the pop-up window and how the visually highlighted media artifact in the pop-up window relates to the media preferences in response to a user action.

21. The non-transitory computer-readable storage medium of claim 20 further comprising: displaying the generated additional information and resources about the visually highlighted media artifact in the pop-up window and how the visually highlighted media artifact relates in the pop-up window to the media preferences in a second pop-up window.

22. The non-transitory computer-readable storage medium of claim 13 wherein the selection comprises a user action selected from the group consisting of mouse movement, mouse clicking, keyboard input and touch input.

* * * * *